(12) United States Patent
Vaughn et al.

(10) Patent No.: US 7,435,598 B2
(45) Date of Patent: Oct. 14, 2008

(54) CATALYST TESTING APPARATUS AND PROCESS

(75) Inventors: Stephen N. Vaughn, Kingwood, TX (US); John K. Pierce, Houston, TX (US); Douglas B. King, Houston, TX (US); Christopher G. Lington, Houston, TX (US)

(73) Assignee: Exxonmobil Chemical Patents Inc., Houston, TX (US)

( * ) Notice: Subject to any disclaimer, the term of this patent is extended or adjusted under 35 U.S.C. 154(b) by 897 days.

(21) Appl. No.: 10/705,036

(22) Filed: Nov. 10, 2003

(65) Prior Publication Data

US 2005/0101022 A1 May 12, 2005

(51) Int. Cl.
*G01N 31/10* (2006.01)
*G01N 1/22* (2006.01)
*B01J 8/00* (2006.01)

(52) U.S. Cl. .......................... 436/37; 422/64; 422/129; 422/130; 422/196; 422/211; 436/43; 436/155; 436/159; 436/161; 436/181

(58) Field of Classification Search .................. 422/64, 422/67, 78, 80, 129, 130, 196, 211; 436/37, 436/43, 155, 159, 161, 181
See application file for complete search history.

(56) References Cited

U.S. PATENT DOCUMENTS

| | | | | |
|---|---|---|---|---|
| 1,601,879 A | * | 10/1926 | Opderbeck | 422/49 |
| 3,431,077 A | * | 3/1969 | Danforth | 422/80 |
| 3,536,452 A | * | 10/1970 | Norton et al. | 422/63 |
| 3,583,230 A | * | 6/1971 | Patterson | 73/864.85 |
| 3,832,140 A | * | 8/1974 | Lorch et al. | 422/65 |
| 4,071,324 A | * | 1/1978 | Reid | 422/78 |
| 4,071,364 A | | 1/1978 | Clark et al. | 96/36 |
| 4,099,923 A | | 7/1978 | Milberger | 25/254 R |
| 4,221,568 A | * | 9/1980 | Boettger | 436/48 |
| 4,533,641 A | * | 8/1985 | Holt | 436/43 |
| 4,600,827 A | * | 7/1986 | Linwood et al. | 219/492 |
| 4,626,412 A | | 12/1986 | Ebner et al. | 422/50 |
| 4,824,790 A | * | 4/1989 | Carangelo et al. | 436/157 |
| 4,837,158 A | | 6/1989 | Toulhoat et al. | 436/37 |
| 4,837,374 A | * | 6/1989 | Brown et al. | 422/130 |
| 4,927,545 A | * | 5/1990 | Roginski | 210/745 |
| 5,039,489 A | | 8/1991 | Gleaves et al. | 422/68.1 |
| 5,358,691 A | | 10/1994 | Clark et al. | 422/64 |
| 5,441,700 A | | 8/1995 | Markelov | 422/83 |

(Continued)

FOREIGN PATENT DOCUMENTS

EP    1 167 967    1/2002

(Continued)

OTHER PUBLICATIONS

Wen, W. Y. et al, Industrial & Engineering Chemistry Process Design and Development 1984, 23, 627-637.*

(Continued)

*Primary Examiner*—Arlen Soderquist

(57) ABSTRACT

An apparatus and process are described in which a plurality of preloaded catalyst samples tubes can be serially and automatically moved from a support to a reaction zone where each catalyst sample can be heated and a preheated reagent feed contacted with the sample and the effluent fed to a product collection and analysis system.

19 Claims, 2 Drawing Sheets

U.S. PATENT DOCUMENTS

| | | | |
|---|---|---|---|
| 5,770,154 A | 6/1998 | Bigeard et al. | 422/80 |
| 5,792,423 A | 8/1998 | Markelov | 422/83 |
| 5,866,072 A * | 2/1999 | Bowe et al. | 422/78 |
| 6,086,832 A | 7/2000 | Ohta | 422/211 |
| 6,087,181 A | 7/2000 | Cong | 436/37 |
| 6,265,226 B1 | 7/2001 | Petro et al. | 436/180 |
| 6,306,658 B1 | 10/2001 | Turner et al. | 436/37 |
| 6,410,332 B1 | 6/2002 | Desrosiers et al. | 436/37 |
| 6,426,226 B1 | 7/2002 | Senkan | 436/37 |
| 6,455,316 B1 | 9/2002 | Turner et al. | 436/37 |
| 6,489,168 B1 | 12/2002 | Wang et al. | 436/37 |
| 6,492,184 B1 | 12/2002 | Petro et al. | 436/180 |
| 6,495,105 B1 | 12/2002 | Yamada et al. | 422/83 |
| 6,497,844 B1 | 12/2002 | Bacaud et al. | 422/68.1 |
| 6,508,984 B1 | 1/2003 | Turner et al. | 422/65 |
| 6,548,026 B1 | 4/2003 | Dales et al. | 422/138 |
| 6,548,305 B1 | 4/2003 | Deves et al. | 436/37 |
| 6,551,832 B1 | 4/2003 | Deves et al. | 436/37 |
| 6,627,881 B1 * | 9/2003 | Bertrand et al. | 250/288 |
| 2002/0182128 A1 | 12/2002 | Carnahan et al. | 422/188 |
| 2003/0003017 A1 | 1/2003 | Frank et al. | 422/68.1 |
| 2003/0012700 A1 | 1/2003 | Carnahan | 422/102 |
| 2003/0040116 A1 * | 2/2003 | Canos et al. | 436/37 |
| 2003/0045000 A1 | 3/2003 | Frank et al. | 436/180 |
| 2003/0064006 A1 | 4/2003 | Carnahan et al. | 422/99 |

FOREIGN PATENT DOCUMENTS

| | | |
|---|---|---|
| EP | 1 256 377 | 11/2002 |
| EP | 1 273 919 | 1/2003 |
| JP | 7-92070 * | 4/1995 |

OTHER PUBLICATIONS

Ellig, D. L. et al, Industrial & Engineering Chemistry Process Design and Development 1985, 24, 1080-1087.*

Mukhopadhyay, R. et al, Industrial & Engineering Chemistry Research 1993, 32, 1914-1920.*

Perez, G. et al, Journal of Analytical and Applied Pyrolysis 1995, 35, 157-166.*

Xanthopoulou, G., Applied Catalysis, A: General 1999, 182, 285-295.*

Samolada, M. C. et al, Energy & Fuels 2000, 14, 1161-1167.*

Jia, J. et al, Catalysis Letters 2001, 76, 183-192.*

Nielsen, C. A. et al, Analytical Chemistry 2002, 74, 3112-3117.*

Jeong, S. M. et al, Catalysis Today 2002, 74, 257-264.*

Hahndorf, I. et al, Chemical Engineering Journal 2002, 89, 119-125.*

* cited by examiner

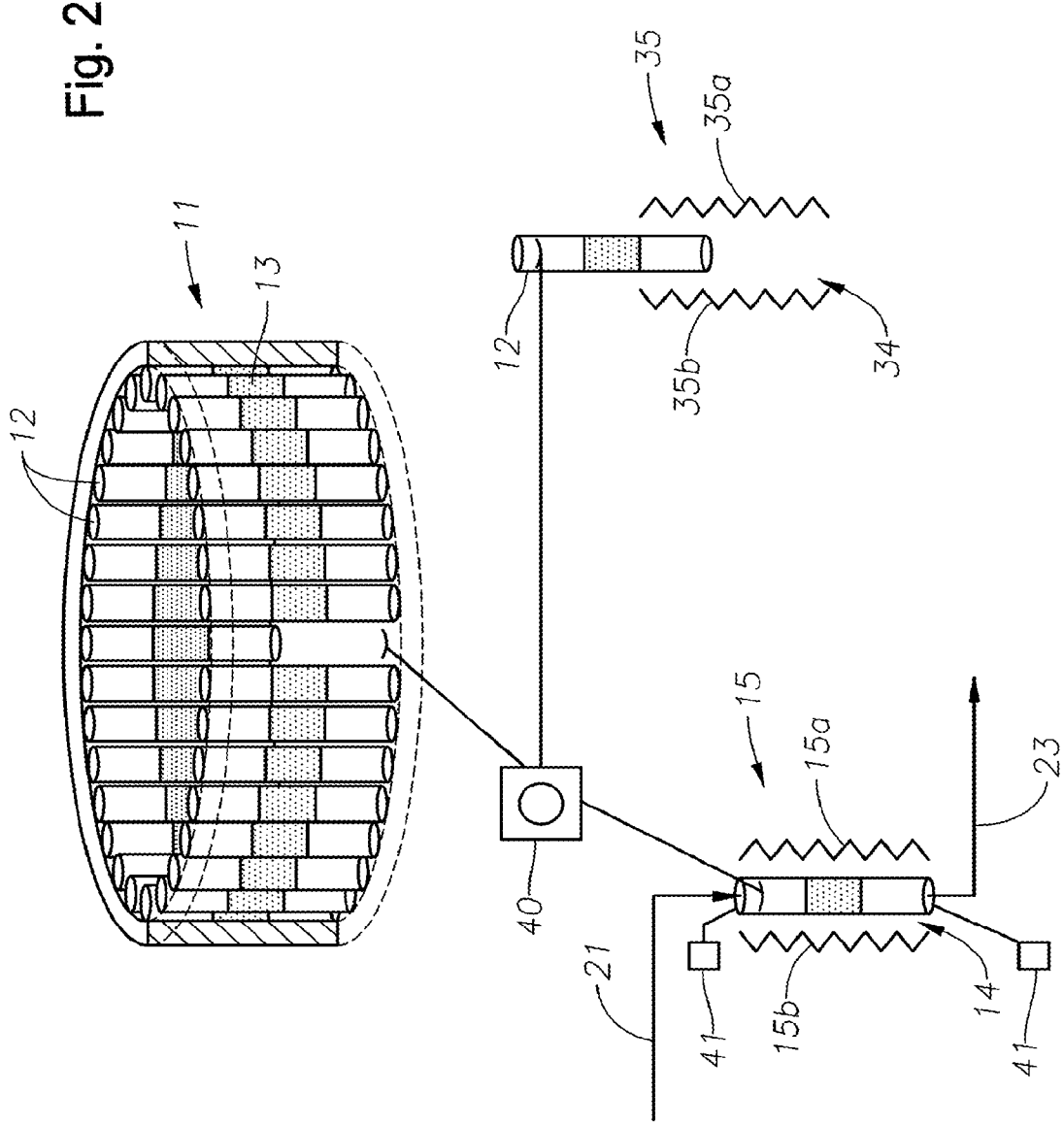

CATALYST TESTING APPARATUS AND PROCESS

FIELD

This invention relates to an apparatus and process for the automatic and sequential testing of a plurality of catalyst samples.

BACKGROUND

In the art of catalysis, there is often little predictability between the composition and/or structure of a material and its catalytic properties. Therefore, essentially the only way to determine if a particular material is a good catalyst is by testing the material under the actual conditions encountered in the process of interest. Moreover, evaluation of a new material for a particular catalytic application requires the material to be tested over a wide range of experimental conditions (such as pressure, flow rates, temperature and concentrations of reagents).

Thus the evaluation of potential catalytic materials requires that a large number of separate tests be performed. This can be time consuming and expensive, not only because of the time required to effect each test but also because of the time required to prepare the catalyst and establish the desired process conditions. Added to this is the challenge that catalytic evaluations must frequently be conducted on very limited quantities of material, particularly where the material is the product of a novel synthesis technique.

To address these problems, a number of automated catalyst testing devices have been developed which typically operate by simultaneously testing a plurality of catalyst samples in a particular process and then sequentially or simultaneously analyzing the products of each test. However, these parallel testing devices frequently require very sophisticated control equipment, valving and analytical equipment that can make the devices extremely expensive.

There is therefore a need for apparatus that can effect rapid and automatic serial testing of a plurality of catalyst samples.

U.S. Pat. No. 4,071,364 discloses an apparatus for contacting a fluid stream with a particulate solid contact material, the apparatus comprising a supported heat exchange body, temperature regulating means surrounding said heat exchange body, a vertically disposed open ended tube extending through said heat exchange body, upper closure means and lower closure means for said tube, a support means attached to said lower closure and extending into said tube and a supply conduit disposed in said heat exchange body opening into said tube above said support means and below said upper closure means. The apparatus allows catalyst to be quickly removed from the bottom of the tube and a new sample added through the top of the tube without losing time in cooling and reheating the reactor. However, relatively large quantities of catalyst are required and catalyst replacement is effected manually.

U.S. Pat. No. 4,099,923 discloses an automatic catalyst screening unit for the parallel, automatic screening of a plurality of potential catalysts comprising a reactor module defining a plurality of elongated reaction chambers for receiving respective potential catalysts; feeding means for individually and selectively feeding each of said reaction chambers with gaseous reactant; and analyzing means for analyzing the product passing out of said reaction chambers, said analyzing means communicating with said plurality of reaction chambers by means of a common manifold.

U.S. Pat. No. 5,441,700 discloses a headspace autosampling apparatus for generating and delivering gaseous samples from headspaces in vials holding substances for analysis to an inlet of an analytical instrument for analysis, the apparatus comprising: a plurality of generally cylindrical vials having an interior area which contains a substance therein, at least a portion of which is liquid and including a headspace above said substance; means for rotating said vials about an axis extending longitudinally through said interior area and wherein said axis extends generally horizontally such that a film of said substance coats an interior surface of the vials whereby the rate of diffusion of the substance into the headspace is increased; holding means for holding the plurality of vials, wherein said holding means holds said vials in a vertically stacked relation and with the longitudinal axis of each vial extending in a generally horizontal direction; heating means for heating a heated zone; means for delivering said vials one at a time from said holding means to the heated zone; and, means for placing the headspace of the vials in said heated zone in fluid communication with said inlet.

U.S. Pat. No. 6,306,658 discloses apparatus for parallel processing of reaction mixtures comprising vessels sealed against fluid communication with one another and adapted for containing the reaction mixtures at pressures different than ambient pressures; a stirring system for agitating the reaction mixtures; a temperature control system for regulating the temperature of the reaction mixtures in the vessels; and an injection system comprising a fluid delivery probe movable from one vessel to another vessel for effecting the introduction of a fluid into each of the vessels at a pressure different than ambient pressure, said injection system being operable for preventing leakage of fluid under pressure from each vessel during said introduction by said fluid delivery probe and after said probe has moved to another vessel.

U.S. Patent Application Publication No. 2003/0003017 discloses a method of parallel screening one or more material properties or one or more characteristics of reaction of two or more samples comprising the steps of: loading one or more library of samples into a reaction chamber; sealing the reaction chamber; and transporting the library of samples to an injection module for injection of one or more chemical components onto the samples comprising each library.

SUMMARY

In one aspect, the present invention resides in apparatus for the sequential testing of a plurality of catalyst samples, the apparatus comprising:

(a) a plurality of reactor tubes into which the catalyst samples can be preloaded;

(b) a support for receiving said preloaded reactor tubes;

(c) a reaction zone;

(d) a programmable device for transporting each of said preloaded reactor tubes sequentially from said support to said reaction zone and for sealing each reactor tube when in said reaction zone;

(e) a heater for heating the catalyst sample in each reactor tube when said tube is in said reaction zone;

(f) means for supplying at least one preheated feed to each preloaded reactor tube when said tube is in said reaction zone; and (g) a product collection and analysis system for collecting and analyzing at least part of any reaction product generated when each preloaded reactor tube is in said reaction zone and said at least one preheated feed is supplied to said reactor tube to contact the heated catalyst sample in said tube.

In one embodiment, said heater is movable between an open position, in which a preloaded reactor tube can be transported by said programmable device into the reaction zone, and a closed position, in which said heater substantially surrounds the tube. Conveniently, the heater is operable to raise the temperature of each reactor tube, when said tube is in said reaction zone, at a rate of at least 20° C./minute, such as at least 50° C./minute.

In one embodiment, said support is a circular carousel which is arranged to support said preloaded reactor tubes around its circumference such that the axes of the tubes are parallel and which is rotatable about an axis parallel to the axis of said tubes. Typically, the carousel is rotatable about a vertical axis.

In a further aspect, the present invention resides in a process for the sequential testing of a plurality of catalyst samples, the process comprising:

(a) loading each of said catalyst samples into a respective reactor tube;

(b) mounting the loaded reactor tubes on a support;

(c) transporting each of said loaded reactor tubes sequentially from said support to a first reaction zone;

(d) sealing each loaded reactor tube when said tube is in said first reaction zone;

(e) heating the catalyst sample loaded in each reactor tube when said tube is in said first reaction zone;

(f) supplying at least one preheated feed to each loaded reactor tube when said tube is in said first reaction zone;

(g) collecting at least part of any reaction product generated when each loaded reactor tube is in said first reaction zone and said at least one preheated feed is supplied to said reactor tube to contact the heated catalyst sample in said tube; and (h) analyzing said reaction product, wherein at least operations (c) to (h) are effected automatically by a computer controlled system.

BRIEF DESCRIPTION OF THE DRAWINGS

FIG. 2 is a schematic illustration showing a portion of the FIG. 1 apparatus setup in greater detail and further illustrating additional elements which may be a part of the testing apparatus herein.

DETAILED DESCRIPTION OF THE EMBODIMENTS

Figure 1:
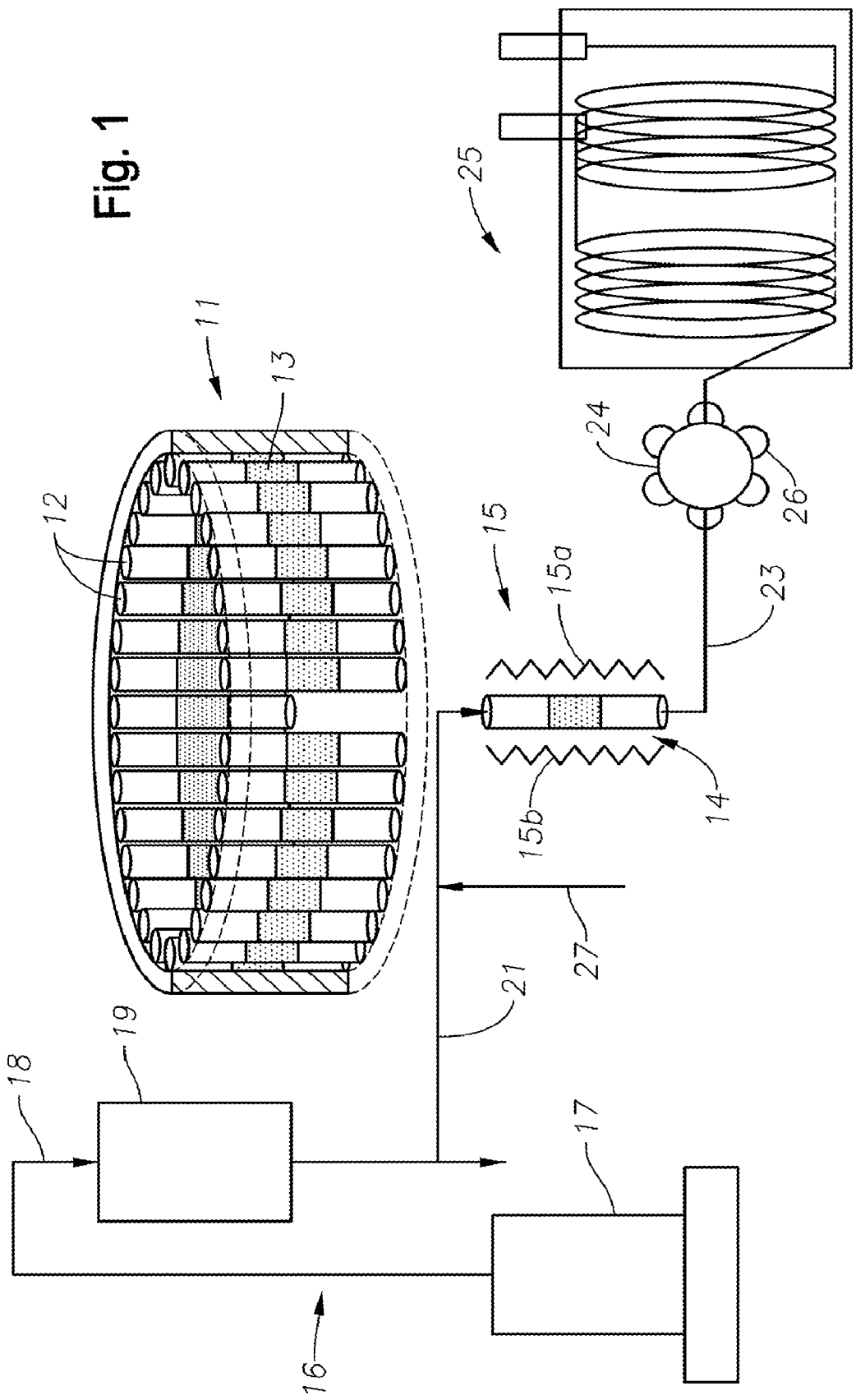
FIG. 1 is a schematic illustration of apparatus according to one example of the invention for the sequential testing of a plurality of catalyst samples.

The present invention provides a simple and inexpensive process and apparatus for sequentially testing a plurality of catalyst samples. Each catalyst sample is initially preloaded into a respective reactor tube, which is conveniently made of an inert material, such as quartz, silica coated stainless steel or the like and the preloaded reactor tubes are then mounted in a support, such as a rotatable carousel. In other instances, metal tubes may be employed if the reaction of the reactant feed on the metal tube is small relative to the reaction effected by the catalyst. The reactor tubes are then serially and automatically moved from the support to a reaction zone where each catalyst sample is heated and then contacted with a preheated reactant feed. Depending on the activity of the sample and the conditions of the test, the preheated feed reacts in the presence of the catalyst sample to produce a reaction product, which is then fed automatically to a product collection and analysis system.

The present process and apparatus are particularly suitable for testing small quantities of catalyst, typically between 5 and 100 mg of catalyst, using reactor tubes having an internal diameter between 2 and 10 mm.

The present process and apparatus can be used to test the activity of any catalyst sample in the catalytic conversion of any reactant or combination of reactants. It is desirable, however, that the reactant(s) is in the form of a vapor when the reactant(s) contacts the catalyst. It is also desirable that the reaction product be recovered in the form of a vapor or at least is in a liquid state such that the liquid can be transported by a carrier gas to the product collection and analysis system. Of course, since the reactant is preheated prior to contacting the catalyst, the preheating can also be used to vaporize the reactant(s). In addition, the apparatus can include an appropriate heater unit in order to vaporize the reaction products so that the system will operate satisfactorily.

Examples of reactants that can be used in this invention include oxygen-containing hydrocarbons such as one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful in the invention include lower straight and branched chain aliphatic alcohols and their unsaturated counterparts. Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. Diluents, such as water and nitrogen, may also be present in the feed. Further examples of reactants that can be used in this invention include hydrocarbons containing one or more alkanes, alkenes, naphthenes, or aromatics containing from 1 to 20 carbon atoms and mixtures thereof. These hydrocarbon reactants may also contain heteroatoms, such as sulfur, nitrogen or oxygen.

A carrier gas may be used to assist in transporting the reactant(s) into the reaction zone and/or in transporting the reaction product from the reaction zone to the product collection and analysis system. The carrier gas can be any type of vapor composition that does not react with the reactant, reaction product or catalyst contained in the reaction zone. In essence, the carrier gas should be inert to the system. Non-limiting examples of suitable carrier gases include helium, argon, nitrogen, carbon monoxide, carbon dioxide, water (in the form of steam), essentially non-reactive paraffins (especially alkanes such as methane, ethane, and propane), essentially non-reactive aromatic compounds, and mixtures thereof.

Catalysts that can be used in the invention are desirably solid catalysts. Any solid catalyst that can be supported in the reaction zone can be readily used. One example of a catalyst that can be used in this invention is a molecular sieve type of catalyst. Non-limiting examples of these molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof, and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of the preferred molecular sieves, particularly for converting an oxygenate containing feedstock into olefin(s), include AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI structure or a CHA structure, or a combination thereof, most preferably a CHA structure.

The reaction zone is desirably maintained at a temperature and pressure at which the reactant and reaction product are in the vapor phase. The reactant is heated prior to contacting the catalyst to a temperature sufficient to have the reactant contact the catalyst in the form of a reaction gas. Any conventional means can be used to heat the reactant. It is desirable to heat the reactant to a temperature of at least 50° C., preferably to a temperature of from about 100° C. to about 800° C. The temperature selected should be in the range that significant reaction occurs due to the action of the catalyst. As is well known to one skilled in the art, excessively high reaction temperatures may lead to undesired thermal reactions that may mask the reactions occurring because of the catalyst and so should be avoided if possible.

The invention will now be more particularly described with reference to FIG. 1, which is a schematic illustration of catalyst testing apparatus according to one example.

Referring to FIG. 1, the apparatus includes a circular, rotatable carousel 11 which is adapted to receive a plurality of open-ended reaction tubes 12 equiangularly-spaced around its periphery such that the axis of each tube is parallel with the axis of rotation of the carousel 11. Typically, the carousel 11 is arranged to receive 30 to 50 reaction tubes 12 and so as to be rotatable about a vertical axis. Prior to being mounted in the carousel 11, each tube 12 is manually preloaded with a catalyst sample 13, conveniently with the sample being sandwiched between porous plugs (not shown).

The carousel 11 is indexable by a motor (not shown) between a plurality of transport positions, in each of which one reaction tube 12 is located adjacent a robot arm (not shown) which is adapted to grip the adjacent reaction tube 12 and transport the tube 12 from the carousel 11 to a reaction zone 14. Located in the reaction zone 14 is a heater 15 and a device (not shown) for sealing and pressure testing each reaction tube 12 when the tube is located in the reaction zone 14. Conveniently, the heater 15 includes two semi-cylindrical heating elements 15a and 15b which are movable between an open position, in which a reactor tube 12 can be transported by the robot arm into the reaction zone 14, and closed position, in which the heater elements 15a, 15b substantially surround the tube 12. Conveniently, the heater 15 is operable to raise the temperature of each reactor tube 12, when said tube is in said reaction zone 14, at a rate of at least 20° C./minute, for example at least 50° C./minute, such as at least 100° C./minute.

Connected to the reaction zone 14 is a reactant supply system 16 that includes a pump 17 for pumping a supply of a suitable reactant, such as methanol, via a line 18 to a heated vaporizer 19. Gas reactant may also be used in which case the reactant supply system 16 would include a device to regulate mass flow of the reactant into the reaction zone. The vaporizer 19 is connected to the reaction zone 14 by a ventable line 21, which in turn is connected to the reaction zone 14 such that, when a reaction tube 12 is located in the reaction zone 14 and is sealed and pressure tested, the line 21 supplies vaporized reactant from the vaporizer 19 to one end of the tube 12.

Also connected to the reaction zone 14 is a product discharge line 23, which in turn is connected through a multiport valve 24 to a product analysis system 25. The discharge line 23 is connected to the reaction zone 14 such that, when a reaction tube 12 is located in the reaction zone 14 and receives vaporized reactant through the line 21, the product of any reaction occurring in the tube 12 flows through the other end of the tube 12 through the line 23 to valve 24. Valve 24 contains one or more sample loops 26 designed to capture, hold and direct one or more samples to the product analysis system 25. The product analysis system 25 includes one or more analytical devices suitable for analyzing some or all of the products and unreacted feed flowing from the reaction tubes 12. Particularly useful analytical devices include a gas chromatograph, a mass spectrometer, an infrared spectrometer and a refractometer.

Operation of the carousel motor, robot arm, heater 15, reactant supply system 16 and valve 24 are controlled by a computer programmed so that the testing of a plurality of catalyst samples loaded in tubes 12 in the carousel 11 occurs automatically and sequentially as follows:

(a) the carousel motor is operated to index the carousel to bring one preloaded reaction tube 12 adjacent the robot arm;

(b) the robot arm is then operated to transport said one tube 12 from the carousel 11 to the reaction zone 14;

(c) the ends of said one tube 12 are then sealed and pressure tested and, assuming the seal is adequate, the heater 15 is switched on to raise the temperature of the catalyst sample in the tube (where sealing integrity can be impacted by high temperature in the reaction zone a leak test is performed after the reaction zone equilibrates to operating temperature);

(d) the reactant supply system 16 is then operated to supply a sample of preheated reactant through line 21 to said one reaction tube 12, preferably such that there is a pressure differential within a predetermined range, typically between about 7 kPa and about 70 kPa, across the catalyst sample;

(e) the valve 24 is then operated to allow some or all of the product generated by any reaction in said one tube to flow, either directly or indirectly, to the product analysis system 25;

(f) the robot arm is then operated to transport said one tube 12 from the reaction zone 14 to the carousel 11; and (g) the cycle of steps (a) to (f) is repeated until all the catalyst samples have been tested.

It will be appreciated that in some cases product analysis may take considerably longer than product generation. Thus, in these instances, the optional sample loops 26 of the valve 24 allow the reaction product from a catalyst sample to be generated and stored, while the reaction product from a previous catalyst sample is being analyzed. In cases where the analysis time is short relative to the reaction time, a least a portion of the product may be directly sampled and analyzed in analysis system 25 without intermediate storage.

In one alternative embodiment, after some or all of the catalyst samples have been tested and their respective reaction tubes 12 have been returned to the carousel 11, each sample is sequentially subjected to one or more further tests. This is effected by sequentially transporting each reactor tube containing the tested catalyst to a second reaction zone, which may be the same or different from the reaction zone 14; sealing and heating each reactor tube when in the second reaction zone; supplying at least one further feed, which may be preheated, to each reactor tube in said second reaction zone; and collecting and analyzing the effluent produced. In FIG. 1, a supply for said further preheated feed is shown at 27. As in the case of the initial series of tests, these additional tests would be computer-controlled. An example of such an additional test could be to measure the amount of coke generated on the catalyst samples during the initial tests, in which case the further feed would conveniently be molecular oxygen containing gas, such as air. Alternatively, the additional tests could involve desorption, metals analysis, chemisorption and/or Temperature Programmed Oxidation (TPO).

Referring to FIG. 2, a portion of the FIG. 1 apparatus is shown in greater detail along with some additional elements which are not shown in FIG. 1. FIG. 2 shows the same carousel 11 holding the same reaction tubes 12 and catalyst samples 13 as are shown in FIG. 1. FIG. 2 also shows the same first reaction zone 14 of FIG. 1 which holds one of the reaction tubes that has been removed from the carousel 11 and placed within the reaction zone 14. The FIG. 2 first reaction zone 14, as in FIG. 1, is also provided with a heater 15 which includes the two semi-cylindrical heating elements 15a and 15b. In FIG. 2, line 21 provides the inflow of vaporized reactant from the reactant supply system shown as system 16 in FIG. 1, but not shown in FIG. 2. Further in FIG. 2, discharge line 23 conveys product sample from the reaction zone 14 to the product analysis system shown as element 25 in FIG. 1, but not shown in Figure 2.

FIG. 2 includes an illustration of an additional element which is a programmable device 40 which serves to move a reaction tube 12 from the carousel 11 to the reaction zone 14 and then either back to the carousel 11 or to a second reaction zone 35. FIG. 2 also includes an illustration of sealing means 41 which serve to seal each reaction tube when it is placed within the reaction zone 14.

As indicated, FIG. 2 also includes an illustration of an optional second reaction zone 34 to which a reaction tube 12 may be transferred after it has been tested in the first reaction zone 14. This second reaction zone 34 includes a heater 35 with heating elements 35a and 35b in analogous fashion to the heater 15 and heating elements 15a and 15b of the first reaction zone 14. The second reaction zone 34 would also be configured with reactant supply and product discharge lines analogous to lines 21 and 23 of the first reaction zone 14 and with tube sealing means analogous to sealing means 41. These analogous elements, however, are not shown in FIG. 2 in association with the second reaction zone 34.

The invention claimed is:

1. Apparatus for the sequential testing of a plurality of catalyst samples, the apparatus comprising:
    (a) a plurality of reactor tubes into which catalyst samples have been preloaded;
    (b) a support for receiving said preloaded reactor tubes;
    (c) a reaction zone;
    (d) a programmable device for transporting each of said preloaded reactor tubes sequentially from said support to said reaction zone and for sealing each reactor tube when in said reaction zone;
    (e) a heater for heating the catalyst sample in each reactor tube when said tube is in said reaction zone;
    (f) means for supplying at least one preheated feed to each preloaded reactor tube when said tube is in said reaction zone; and
    (g) a product collection and analysis system for collecting and analyzing at least part of any reaction product generated when each preloaded reactor tube is in said reaction zone and said at least one preheated feed is supplied to said reactor tube to contact the heated catalyst sample in said tube,
    wherein said heater is movable between an open position, in which a preloaded reactor tube can be transported by said programmable device into the reaction zone, and a closed position, in which said heater substantially surrounds the tube.

2. The apparatus of claim 1 wherein said heater is operable to raise the temperature of each preloaded reactor tube, when said tube is in said reaction zone, to a temperature of at least 50° C. to about 800° C., at a rate of at least 20° C./minute.

3. The apparatus of claim 1 wherein said heater is operable to raise the temperature of each preloaded reactor tube, to a temperature of at least 50° C. to about 800° C., when said tube is in said reaction zone, at a rate of at least 50° C./minute.

4. The apparatus of claim 1 wherein said support is a circular carousel which is arranged to support said preloaded reactor tubes around its circumference such that the axes of the tubes are parallel and which is rotatable about an axis parallel to the axis of said tubes.

5. The apparatus of claim 4 wherein the carousel is rotatable around a vertical axis.

6. The apparatus of claim 1 wherein said product collection and analysis system includes a multi-port valve connected to one or more storage units for temporarily storing the reaction product from a tested catalyst sample.

7. Apparatus for the sequential testing of a plurality of catalyst samples, the apparatus comprising:
    (a) a plurality of reactor tubes into which catalyst samples have been preloaded;
    (b) a support for receiving said preloaded reactor tubes;
    (c) a reaction zone;
    (d) a programmable device for transporting each of said preloaded reactor tubes sequentially from said support to said reaction zone and for sealing each reactor tube when in said reaction zone;
    (e) a heater for heating the catalyst sample in each reactor tube when said tube is in said reaction zone;
    (f) means for supplying at least one preheated feed to each preloaded reactor tube when said tube is in said reaction zone; and
    (g) a product collection and analysis system for collecting and analyzing at least part of any reaction product generated when each preloaded reactor tube is in said reaction zone and said at least one preheated feed is supplied to said reactor tube to contact the heated catalyst sample in said tube,
    and further including a pressure control system which is operable when each preloaded reactor tube is transported into the reaction zone:
    (i) to test the seal of reactor tube;
    (ii) to increase the pressure in each reactor tube when the test (i) has shown that the tube is sealed; and
    (iii) to generate a predetermined pressure drop across the catalyst sample in the reactor tube.

8. A process for the sequential testing of a plurality of catalyst samples, the process comprising:
    (a) loading each of said catalyst samples into a respective reactor tube;
    (b) mounting the loaded reactor tubes on a support;
    (c) transporting each of said loaded reactor tubes sequentially from said support to a first reaction zone;
    (d) sealing each loaded reactor tube when said tube is in said first reaction zone;
    (e) heating the catalyst sample loaded in each reactor tube when said tube is in said first reaction zone;
    (f) supplying at least one preheated feed to each loaded reactor tube when said tube is in said first reaction zone to produce a reaction product, by virtue of contact of preheated feed with catalyst in said tube;
    (g) collecting at least part of said reaction product generated when each loaded reactor tube is in said first reaction zone and said at least one preheated feed is supplied to said reactor tube to contact the heated catalyst sample in said tube;
    (h) analyzing said reaction product,
    (i) after (g), sequentially transporting each reactor tube containing the tested catalyst to a second reaction zone;
    (j) sealing each reactor tube when said tube is in said second reaction zone;
    (k) heating each reactor tube when said tube is in said second reaction zone;

(l) supplying at least one further preheated feed to each reactor tube when said tube is in said second reaction zone;

(m) collecting at least part of the effluent generated when each reactor tube is in said second reaction zone and said at least one further preheated feed is supplied to said reactor tube to contact the catalyst sample in said tube; and (n) analyzing said effluent, wherein at least operations (c) to (h) are effected automatically by a computer controlled system, wherein at least operations (i) to (n) are effected automatically by a computer controlled system, and wherein:

each reactor tube containing the tested catalyst is returned to said support and is then sequentially transported from said support to said second reaction zone, or said second reaction zone is different from said first reaction zone.

9. The process of claim 8 wherein said heating is conducted to a temperature of at least 50° C. to about 800° C., at a rate of at least 20° C./minute.

10. The process of claim 8 wherein said heating is conducted to a temperature of at least 50° C. to about 800° C., at a rate of at least 50° C./minute.

11. The process of claim 8 wherein at least one of the plurality catalyst samples includes a molecular sieve catalyst.

12. The process of claim 8 wherein said feed includes a hydrocarbon.

13. The process of claim 12 wherein said hydrocarbon includes an olefin, aromatic compound, alkane or mixture thereof.

14. The process of claim 12 wherein said feed include a heteroatom.

15. The process of claim 14 wherein said heteroatom includes sulfur, nitrogen or oxygen.

16. The process of claim 14 wherein said feed includes an organic oxygenate.

17. The process of claim 16 wherein said organic oxygenate includes an alcohol having 1 to 4 carbon atoms.

18. The process of claim 8 wherein said feed includes molecular oxygen.

19. The process of claim 8 wherein said second reaction zone is the same as said first reaction zone.

* * * * *